US009599582B2

(12) United States Patent
Fargo et al.

(10) Patent No.: US 9,599,582 B2
(45) Date of Patent: Mar. 21, 2017

(54) SIMPLIFIED RESISTANCE BASED BELT INSPECTION (71) Applicants: Richard N. Fargo, Plainville, CT (US); Peter Liaskas, Norwalk, CT (US)

(72) Inventors: Richard N. Fargo, Plainville, CT (US); Peter Liaskas, Norwalk, CT (US)

(73) Assignee: OTIS ELEVATOR COMPANY, Farmington, CT (US)

(*) Notice: Subject to any disclaimer, the term of this patent is extended or adjusted under 35 U.S.C. 154(b) by 239 days.

(21) Appl. No.: 13/782,788

(22) Filed: Mar. 1, 2013

(65) Prior Publication Data

US 2013/0207668 A1  Aug. 15, 2013

Related U.S. Application Data (63) Continuation-in-part of application No. PCT/US2010/047445, filed on Sep. 1, 2010.

(51) Int. Cl.
*G01R 27/14* (2006.01)
*G01N 27/20* (2006.01)
(Continued)

(52) U.S. Cl.
CPC ........... *G01N 27/20* (2013.01); *B66B 7/1223* (2013.01); *D07B 1/145* (2013.01); *G01N 27/046* (2013.01); *G01R 35/00* (2013.01); *H01C 1/16* (2013.01)

(58) Field of Classification Search
CPC .................................................... G01R 27/14
See application file for complete search history.

(56) References Cited

U.S. PATENT DOCUMENTS 5,307,672 A * 5/1994 Macchiarulo et al. .... 73/114.77
5,834,942 A   11/1998 De Angelis
(Continued)

FOREIGN PATENT DOCUMENTS

EP  1357073 A1  10/2003
EP  1362001 B1  2/2006
(Continued)

OTHER PUBLICATIONS

Japanese Office Action, Application No. 2013/527047 dated on Apr. 16, 2014.
(Continued)

*Primary Examiner* — Jermele M Hollington
*Assistant Examiner* — Feba Pothen
(74) *Attorney, Agent, or Firm* — Cantor Colburn LLP (57) ABSTRACT A resistance circuit for monitoring a support structure is provided. The resistance circuit may include a first set of resistors disposed at a belt-side and a second set of resistors disposed at a monitor-side. The first set of resistors may be configured to indicate one or more voltages thereacross corresponding to an effective resistance of the support structure. The first set of resistors may include at least one temperature-dependent resistor. The second set of resistors may be configured to indicate one or more voltages thereacross corresponding to an initial effective resistance of the support structure. The second set of resistors may include at least one switched resistor having an adjustable resistance capable of selectively approximating the initial effective resistance.

19 Claims, 10 Drawing Sheets (51) Int. Cl.
*H01C 1/16* (2006.01)
*G01R 35/00* (2006.01)
*G01N 27/04* (2006.01)
*D07B 1/14* (2006.01)
*B66B 7/12* (2006.01)

(56) References Cited

U.S. PATENT DOCUMENTS

| | | | |
|---|---|---|---|
| 5,886,308 A | 3/1999 | Ericson et al. | |
| 5,890,564 A | 4/1999 | Olsen et al. | |
| 5,992,574 A | 11/1999 | Olsen et al. | |
| 6,073,728 A | 6/2000 | Olsen et al. | |
| 6,082,122 A * | 7/2000 | Madenokouji et al. | 62/77 |
| 6,123,176 A | 9/2000 | O'Donnell et al. | |
| 6,289,742 B1 | 9/2001 | De Angelis | |
| 6,422,088 B1 * | 7/2002 | Oba et al. | 73/754 |
| 6,633,159 B1 | 10/2003 | Robar et al. | |
| 6,653,943 B2 | 11/2003 | Lamb et al. | |
| 6,684,981 B2 | 2/2004 | Stucky et al. | |
| 6,886,666 B2 | 5/2005 | Stucky et al. | |
| 6,943,576 B2 * | 9/2005 | Byun et al. | 324/762.03 |
| 7,117,981 B2 | 10/2006 | Logan et al. | |
| 7,123,030 B2 | 10/2006 | Robar et al. | |
| 7,409,870 B2 | 8/2008 | Stucky et al. | |
| 7,410,033 B2 | 8/2008 | Veronesi et al. | |
| 7,506,728 B2 | 3/2009 | Hawkes et al. | |
| 7,540,359 B2 | 6/2009 | Veronesi et al. | |
| 8,337,082 B2 * | 12/2012 | Coursey et al. | 374/185 |
| 8,813,918 B2 * | 8/2014 | Kocher et al. | 187/391 |
| 9,423,369 B2 | 8/2016 | Fargo et al. | |
| 2002/0194935 A1 | 12/2002 | Clarke et al. | |
| 2003/0124417 A1 * | 7/2003 | Bertness et al. | 429/90 |
| 2004/0046540 A1 | 3/2004 | Robar et al. | |
| 2004/0053695 A1 * | 3/2004 | Mattice et al. | 463/42 |
| 2005/0116910 A1 * | 6/2005 | Lee et al. | 345/87 |
| 2007/0168159 A1 | 7/2007 | Veronesi et al. | |
| 2007/0170012 A1 | 7/2007 | Stucky | |
| 2007/0181385 A1 | 8/2007 | Veronesi et al. | |
| 2008/0202863 A1 | 8/2008 | Rossignol et al. | |
| 2008/0223668 A1 | 9/2008 | Stucky et al. | |

FOREIGN PATENT DOCUMENTS

| | | |
|---|---|---|
| EP | 2172410 A2 | 7/2010 |
| JP | H 06286957 A | 10/1994 |
| JP | 06286957 | 11/1994 |
| JP | 8-261972 | 10/1996 |
| JP | H1179589 A | 3/1999 |
| JP | 2002348068 A | 12/2002 |
| JP | S62146889 A | 7/2008 |
| JP | 2009-143678 | 2/2009 |
| JP | 2009/132482 | 6/2009 |
| KR | 100846944 B1 | 7/2008 |
| WO | WO 00/058706 | 10/2000 |
| WO | WO 00/58706 A2 | 10/2000 |
| WO | WO 02/46082 A1 | 6/2002 |
| WO | WO 02/062695 A1 | 8/2002 |
| WO | WO 2005/094248 A2 | 10/2005 |
| WO | WO 2005/095250 A1 | 10/2005 |
| WO | WO 2005/097651 A2 | 10/2005 |
| WO | WO 2008/140520 A1 | 11/2008 |

OTHER PUBLICATIONS

International Search Report and Written Opinion for related International Application No. PCT/US2010/047445; report dated May 30, 2011.

* cited by examiner

| Output Node | Operational State | Thresholds | Interface Output |
|---|---|---|---|
| 44g | [Reference] | [--] | [--] |
| 44f | Shorted State | V(44f) > V(44g) | Alarm / Red LED |
| 44e | Normal State | V(44e) < V(44g) | Green LED |
| 44d | Normal State | V(44d) > V(44g) | Green LED |
| 44c | Low-wear State | V(44c) < V(44g) | Yellow LED |
| 44b | End-of-life State | V(44b) < V(44g) | Alarm / Red LED |
| 44a | Open-circuit or High-wear State | V(44a) < V(44g) | Alarm / Red LED |

SIMPLIFIED RESISTANCE BASED BELT INSPECTION

CROSS-REFERENCE TO RELATED APPLICATION

This application is a continuation-in-part of PCT International Application No. PCT/US10/47445, filed on Sep. 1, 2010.

FIELD OF THE DISCLOSURE

The present disclosure generally relates to monitoring systems and methods, and more particularly, to systems and methods for monitoring the condition of a support structure, for example a belt used in an elevator system.

BACKGROUND OF THE DISCLOSURE

Tensile support structures, such as coated steel belts or wire ropes containing metal cords, are used to move an elevator car up and down within an elevator shaft or hoistway. Because the condition of the tensile support structure is critical to the safety of the operation of the elevator, there is a need to determine the remaining strength level of the tensile support and detect if the remaining strength level falls below a minimum threshold.

The strength of a tensile support structure can be reduced by normal operation of the elevator over time. The primary source of the degradation in the strength of the support structure is the cyclic bending of the support structure around sheaves as the elevator is moved up and down in an elevator shaft or hoistway. The degradation of a support structure is normally not uniform along the length of the support structure, but rather, focused to areas of the support structure that are subjected to high levels or severities of bending cycles.

Some electrical characteristics, such as electrical resistance or impedance, of the cables, cords or tension members in the support structure will vary as the cross-sectional areas of the tension members decrease. Accordingly, it is possible to determine the remaining support strength of the support structure based on the electrical characteristics of the tension members thereof. There currently are some monitoring systems which employ a resistance-based inspection scheme to monitor the resistance of support structures, and thus, the remaining strength thereof. Such systems are built upon microprocessor based designs, which utilize several analog to digital and/or digital to analog interfaces, and other added implementations for processing digital signals. The digital nature of such systems further rely on sampled data, and thus, are unable to provide continuous monitoring or immediate responses to detected fault conditions.

Accordingly, there is a need for a system and method for monitoring that is less complex and more cost-effective. Alternatively or in addition, there is a need for systems and methods that are capable of providing continuous monitoring of support structures and immediate response to detected fault conditions. Finally, there is an alternative or additional need for a monitoring system that allows for easier and more accurate calibrations thereof.

SUMMARY OF THE DISCLOSURE

In accordance with one aspect of the disclosure, a resistance circuit for monitoring a support structure is provided. The resistance circuit may include a first set of resistors disposed at a belt-side of the structure and a second set of resistors disposed at a monitor-side of the structure. The first set of resistors may be configured to indicate one or more voltages thereacross corresponding to an effective resistance of the support structure. The first set of resistors may include at least one temperature-dependent resistor. The second set of resistors may be configured to indicate one or more voltages thereacross corresponding to an initial effective resistance of the support structure. The second set of resistors may include at least one switched resistor having an adjustable resistance capable of selectively approximating the initial effective resistance.

In accordance with another aspect of the disclosure, a monitoring system for a support structure is provided. The monitoring system may include a resistance circuit coupled to the support structure, and an interface circuit having one or more comparators coupled to the resistance circuit. The resistance circuit may include a first set of resistors and at least one temperature-dependent resistor disposed on a belt-side, and a second set of resistors and at least one switched resistor on a monitor-side. The interface circuit may be configured to monitor a wear level of the support structure based on a comparison between a voltage across at least one of the first resistors and a reference voltage across at least one of the second resistors corresponding to an initial effective resistance of the support structure, and generate one or more output signals based on the comparison.

In accordance with yet another aspect of the disclosure, a method for calibrating a resistance-based monitoring system for a support structure is provided. The method may comprise the steps of configuring a resistance circuit that is coupled to the support structure to provide a first set of resistors and at least one temperature-dependent resistor disposed on a belt-side, and a second set of resistors and a plurality of series-connected switched resistors on a monitor-side; and for each consecutive one of the series-connected switched resistors, enabling the series-connected switched resistor, comparing a resistance on the belt-side of the resistance circuit with a resistance on the monitor-side of the resistance circuit, the belt-side resistance corresponding to an effective resistance of the support structure, enabling a consecutive one of the series-connected switched resistors if the belt-side resistance is greater than the monitor-side resistance, and enabling a consecutive one of the series-connected switched resistors and disabling the series-connected switched resistor if the belt-side resistance is less than the monitor-side resistance.

These and other aspects of this disclosure will become more readily apparent upon reading the following detailed description when taken in conjunction with the accompanying drawings.

While the present disclosure is susceptible to various modifications and alternative constructions, certain illustrative embodiments thereof have been shown in the drawings and will be described below in detail. It should be understood, however, that there is no intention to be limited to the specific forms disclosed, but on the contrary, the intention is to cover all modifications, alternative constructions, and equivalents falling with the spirit and scope of the present disclosure.

DETAILED DESCRIPTION

Figure 1:
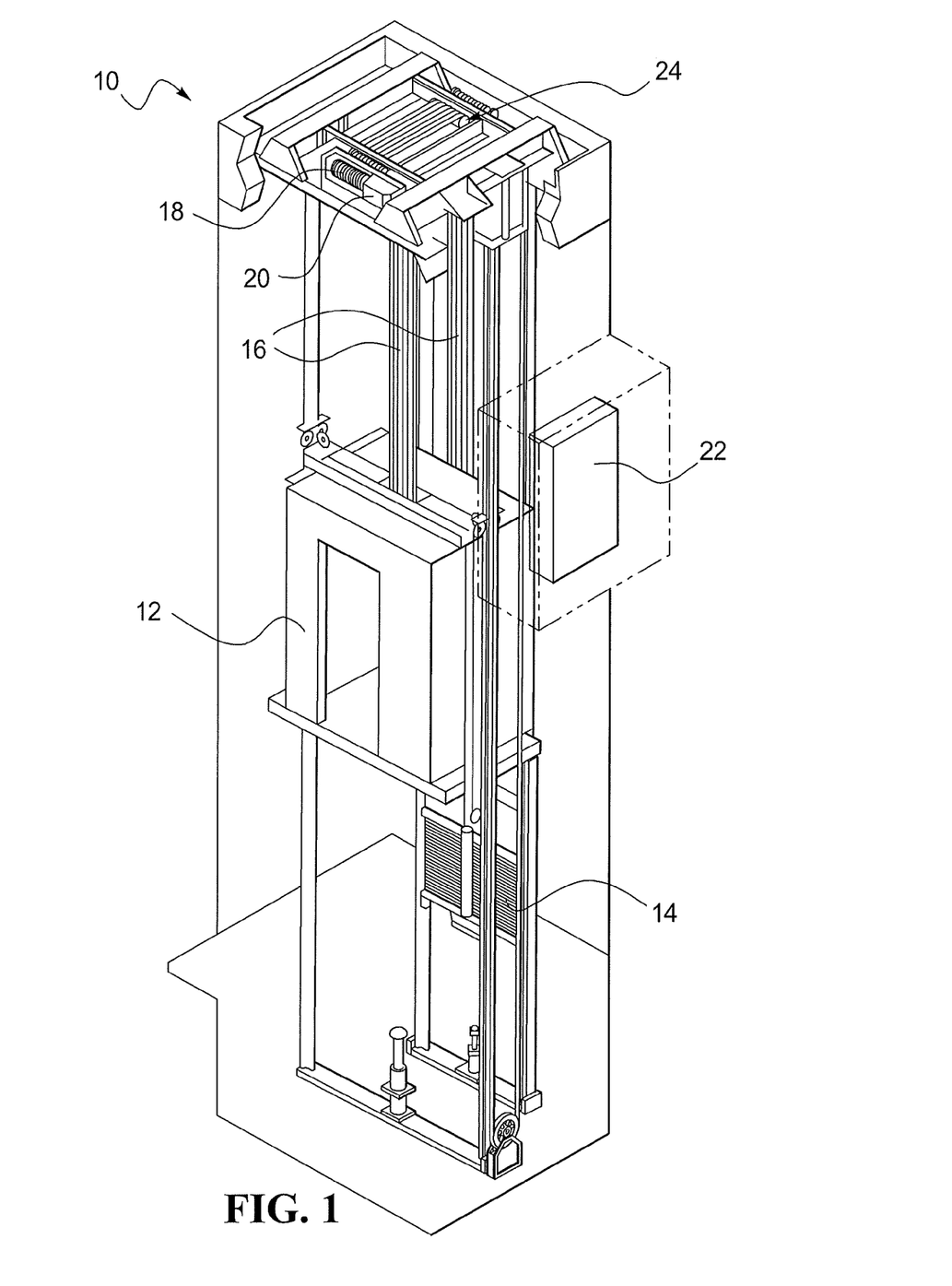
FIG. 1 is a partial perspective view of an elevator system.

The present invention relates to monitoring of support structures. While FIG. 1 describes one possible support structure, in particular a tensile support structure, namely belts or ropes used to suspend and/or drive components of an elevator system, the present invention could be used with other support structures. Other exemplary support structures include belts or jacketed cords as used in exercise machines, jacketed cables as used with cranes, or any other multi-strand wire or rope being used in tension. Referring now to FIG. 1, an elevator system 10 is shown in schematic fashion. It is to be understood that the version of the elevator system 10 shown in FIG. 1 is for illustrative purposes only and to present background for the various components of a general elevator system.

As shown in FIG. 1, the elevator system 10 may include a car 12 coupled to a counterweight 14 by a support structure 16. The support structure 16 may extend over a traction sheave 18 that is driven by a machine 20. Traction between the sheave 18 and the support structure 16 may drive the car 12 and counterweight 14 through the hoistway. Operation of the machine 20 may be controlled by a main controller 22. The elevator system 10 may further include a monitoring system 24 in electrical communication with, and/or disposed in a location proximate to, the support structure 16 and configured to detect the condition of the support structure 16 by measuring, for example continuously or intermittently, the resistance thereof.

Figure 2A:
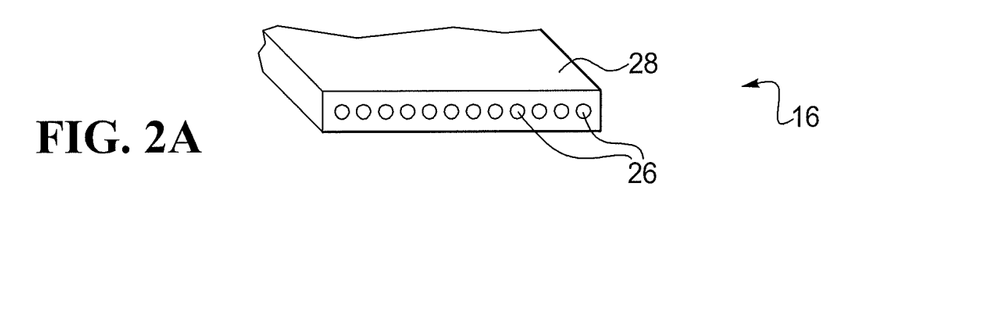
FIG. 2A is a partial perspective view of a tensile support structure.
Figure 2B:
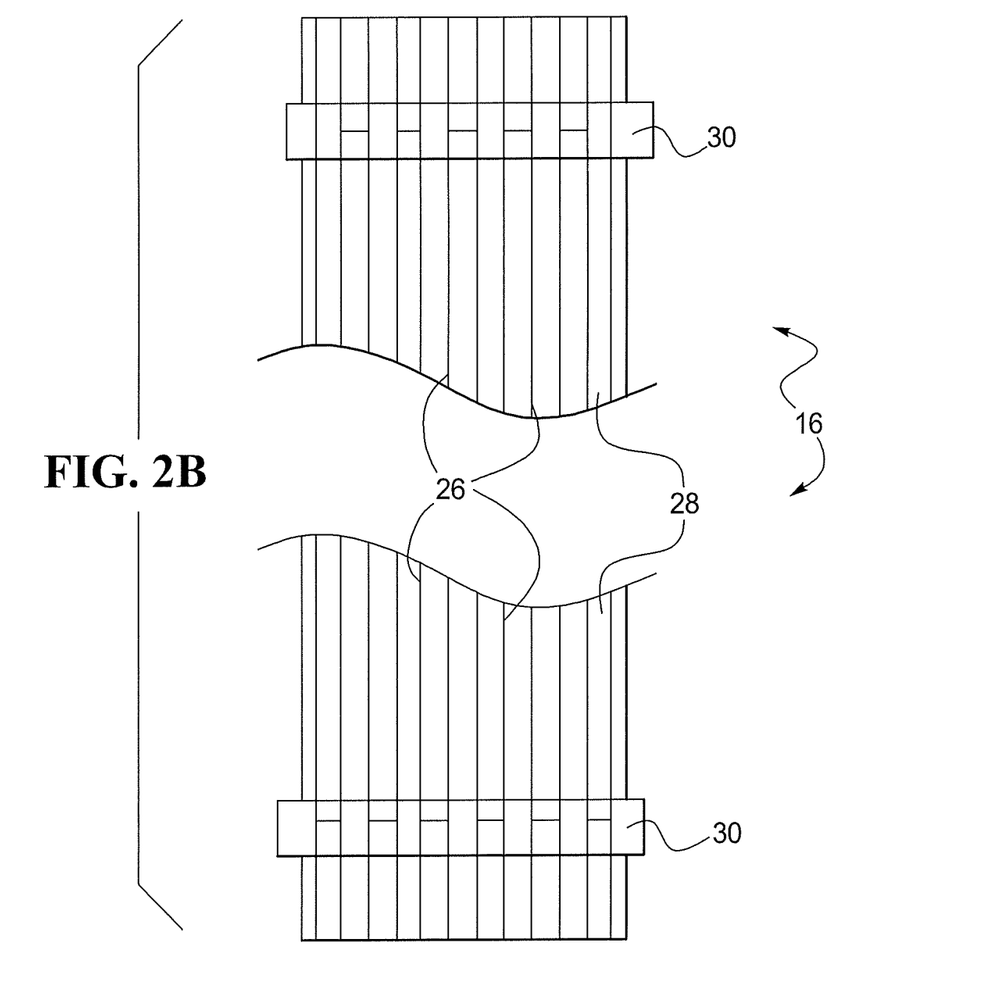
FIG. 2B is partial top plan view of two ends of a tensile support structure.

Turning to FIG. 2A, one exemplary support structure 16 is provided in the form of a belt having a plurality of individual tension members 26 in a jacket coating 28. The tension members 26 may include conventional steel wires formed into strands and/or cords, or any other supportive material having an electrical resistance. The jacket coating 28 may comprise one or more materials suitable for promoting traction with the traction sheave 18, such as polyurethane or elastomeric materials. The jacket coating 28 may additionally comprise an electrically insulative material suitable for prohibiting electrical communication therein. The operational condition or state of one or more (including each) tension member 26 of the support structure 16 of FIG. 2A may be determined using a resistance-based inspection scheme, wherein, for example, the remaining life of the one or more tension members 26 of the support structure 16 may be determined in terms of the increase in the resistance of the tension members 26 relative to a baseline value (for example measured during initial installation of the support structure 16 in the elevator system 10. The overall operational condition or state of a support structure 16 could be monitored continuously or intermittently for any substantial increase in resistance. The support structure 16 may also be monitored for any wear in the jacket coating 28 by, for example, detecting for any contact or electrical short between exposed tension members 26 and electrically conductive idler or fraction sheaves 18. In one possible arrangement, the individual tension members 26 may be connected in series so as to minimize the number of monitored resistances and provide one effective resistance per support structure 16. The effective resistance of a support structure 16 may be indicative of the actual resistance, or any multiple, fraction or scale thereof, exhibited by the support structure 16. As shown by the ends of an exemplary support structure 16 of FIG. 2B, the tension members 26 may be coupled or shorted together at alternating and respective ends using connectors 30 so as to electrically connect the tension members 26 associated with one support structure 16 in series form. Other arrangements, such as monitoring one or more tension members 26 in parallel or a combination of parallel and serial monitoring of subsets of the tension members 26, are also possible.

Figure 3:
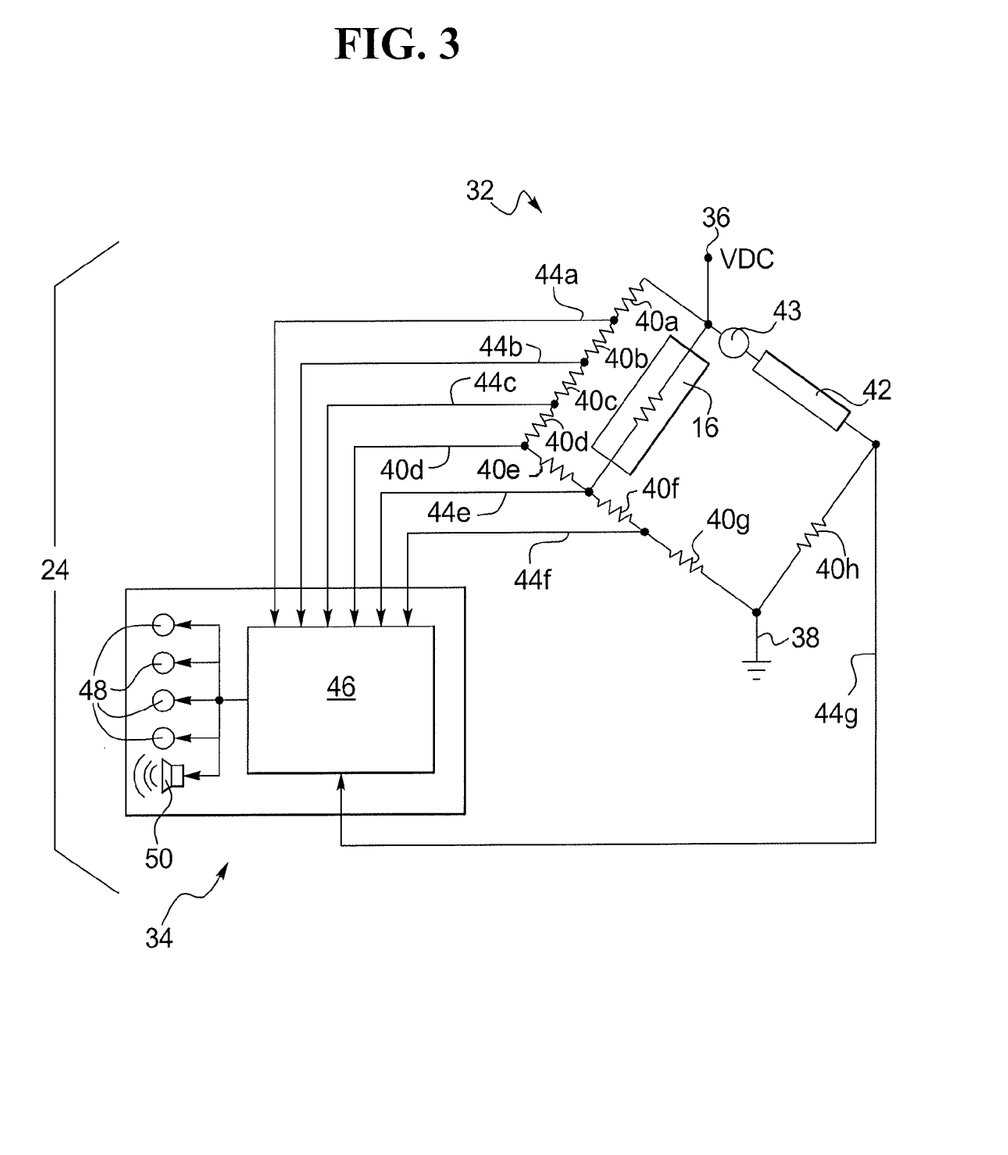
FIG. 3 is a schematic view of one exemplary monitoring system having one type of resistance circuit.

Referring now to FIG. 3, one exemplary system 24 for monitoring the wear condition of a support structure 16 of an elevator system 10 is provided. While other configurations may exist, the monitoring system 24 of FIG. 3 may include a resistance circuit 32 and an interface circuit 34 which employ a resistance-based inspection scheme. The monitoring system 24 may supply an electrical signal through the one or more tension members 26 of a support structure 16 and monitor for any changes in the electrical signal that may be indicative of an increase in resistance or wear. In the particular embodiment of FIG. 3, for example, the resistance circuit 32 may be configured to supply a direct current (DC) voltage across the support structure 16 and the interface circuit 34 may be configured to continuously monitor for changes in the electric current flowing through the support structure 16. Alternatively, the circuit 34 could intermittently monitor for changes in the electric current flowing through the support structure.

As shown in FIG. 3, the resistance circuit 32 may be configured to supply a voltage across the support structure 16 via a voltage input node 36 and a ground node 38 so as to induce an electrical current therethrough. The resistance circuit 32 may further provide a first set of resistors 40 on the belt-side of the resistance circuit 32, as well as a second set of resistors 41, 42 on the reference-side of the resistance circuit 32 that are electrically coupled to the support structure 16 and generally arranged in a voltage divider configuration. For example, the first set of resistors 40 may provide output voltages on the belt-side at output nodes 44a-f which gradually increase or decrease as the support structure 16 wears over time, while the second set of resistors 41, 42 may provide a reference voltage on the reference-side at output node 44g which remains constant until the next calibration. By comparing the output voltages provided by the first set of resistors 40 on the belt-side to the reference voltage provided by the second set of resistors 41, 42 on the reference-side, it may be possible to determine an operational condition or state of the support structure 16.

Still referring to the resistance circuit 32 of FIG. 3, resistors 40a-e may be disposed in parallel to the support structure 16 while resistors 40f-g may be disposed in series to resistors 40a-e and the support structure 16. Resistors 40a-e may be configured with relatively high resistances so as to minimize its effect on the current flowing through the support structure 16. Resistors 40f-g may be disposed substantially parallel to resistor 41, and further, configured to match the resistance thereof. Accordingly, the second set of resistors 41, 42 may be configured to substantially match the effective resistance of the support structure 16, for example, during an initial calibration of the monitoring system 24, so as to provide the baseline or reference voltage to which the output voltages at output nodes 44a-f may be compared. As further shown in FIG. 3, the second set of resistors 41, 42 may also include one or more temperature-dependent resistors 43, such as resistive thermal devices (RTDs), or the like, having a resistance that varies with temperature so as to substantially match any changes in the effective resistance of the support structure 16 caused by changes in ambient temperature. The one or more temperature-dependent resistors 43 may be disposed in substantial series relative to the second set of resistors 41, 42, as shown for example in FIG. 3, or in any other suitable configuration. In further alternative embodiments, the resistor circuit 32 may provide a reference voltage at output node 44g using a pulse-width modulation (PWM) device, or any other suitable means for providing a reference voltage that can be set during calibration.

Figure 4:
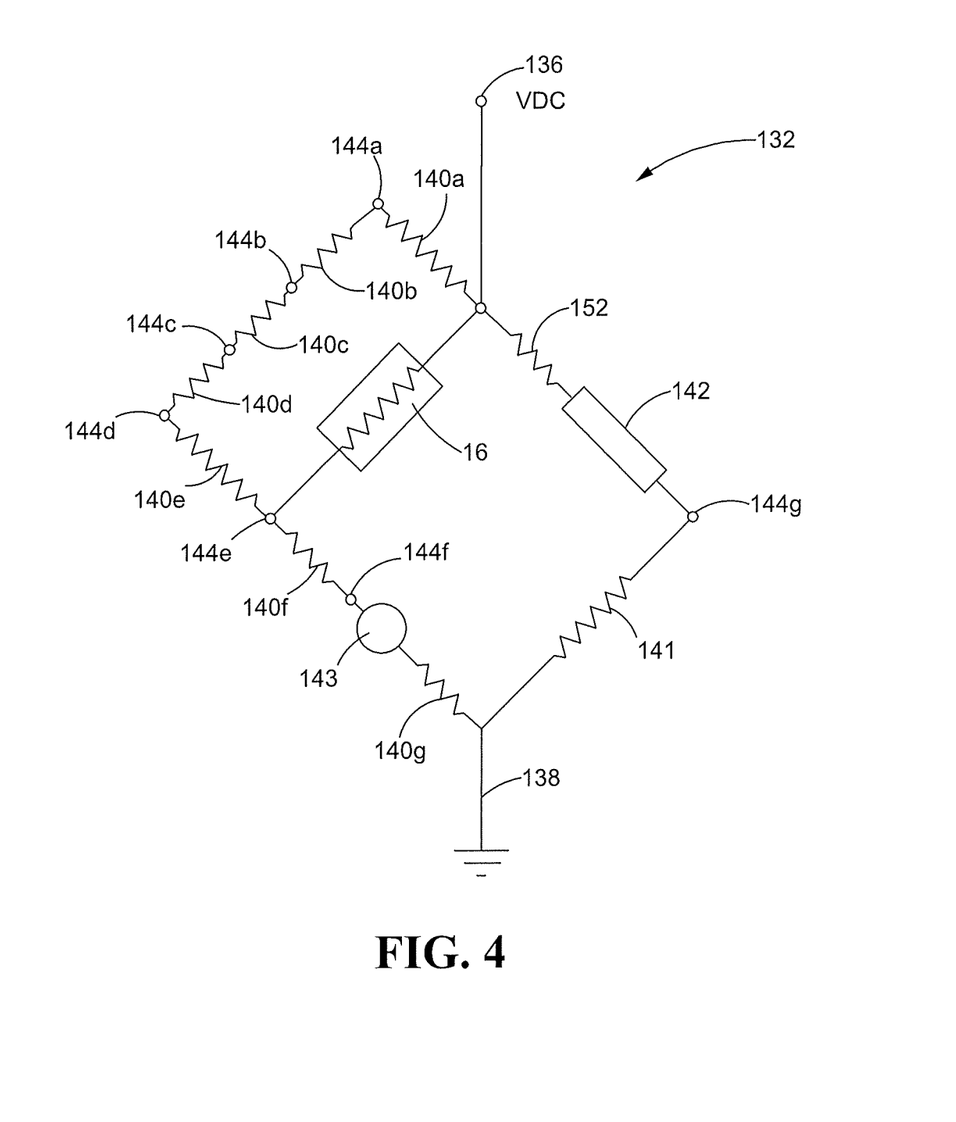
FIG. 4 is a schematic view of another resistance circuit.

Turning to FIG. 4, another resistance circuit 132 which may employ a resistance-based inspection scheme in association with, for example, the system 24 of FIG. 3 for monitoring the wear condition of a support structure 16 of an elevator system 10 is provided. Similar to the previous embodiment of FIG. 3, the resistance circuit 132 of FIG. 4 may be configured to supply a direct current (DC) voltage across the support structure 16 and an associated interface circuit 34 may be configured to continuously or periodically monitor for changes in the electric current flowing through the support structure 16. Moreover, the resistance circuit 132 may be configured to supply a voltage across the support structure 16 via a voltage input node 136 and a ground node 138 so as to induce an electrical current therethrough. The resistance circuit 132 may further provide a first set of resistors 140 on the belt-side of the resistance circuit 132, as well as a second set of resistors 141, 142, 152 on the reference-side of the resistance circuit 132 that are electrically coupled to the support structure 16 and generally arranged in a voltage divider configuration. For example, the first set of resistors 140 may provide output voltages on the belt-side at output nodes 144a-f which gradually increase or decrease as the support structure 16 wears over time, while the second set of resistors 141, 142, 152 may provide a reference voltage on the reference-side at output node 144g which remains constant until the next calibration. By comparing the output voltages provided by the first set of resistors 140 on the belt-side to the reference voltage provided by the second set of resistors 141, 142, 152 on the reference-side, it may be possible to determine an operational condition or state of the support structure 16 based on the change in the effective resistance thereof.

In the resistance circuit 132 of FIG. 4, resistors 140a-e may be disposed in parallel to the support structure 16 while resistors 140f-g may be disposed in series to resistors 140a-e and the support structure 16. Resistors 140a-e may be configured with relatively high resistances so as to minimize its effect on the current flowing through the support structure 16. Belt-side resistors 140f-g may be disposed substantially parallel to resistor 141 on the monitor-side, and further, configured to generally match the resistance thereof. The combination of the additional resistor 152 and resistor 142 may be configured to substantially match the anticipated resistance of the belt or support structure 16. More particularly, the sum of the resistances of the second set of resistors 142, 152 may be configured to substantially match the effective resistance of the support structure 16, for instance, during an initial calibration of the monitoring system 24, so as to provide the baseline or reference voltage to which the output voltages at output nodes 144a-f may be compared. Still further, the temperature-dependent resistor 143 may be positioned on the belt-side rather than on the monitor-side as in the embodiment of FIG. 3 so as to better compensate for changes in the effective resistance of the support structure 16 caused solely by changes in ambient temperature. More specifically, by placing the temperature-dependent resistor 143 on the belt-side and in series between the fixed-resistance resistors 140f and 140g, the temperature-dependent resistor 143 together with the fixed-resistance resistors 140f and 140g may be able to more effectively match the temperature coefficient of the tension members 26 within the belt or support structure 16.

Figure 5:
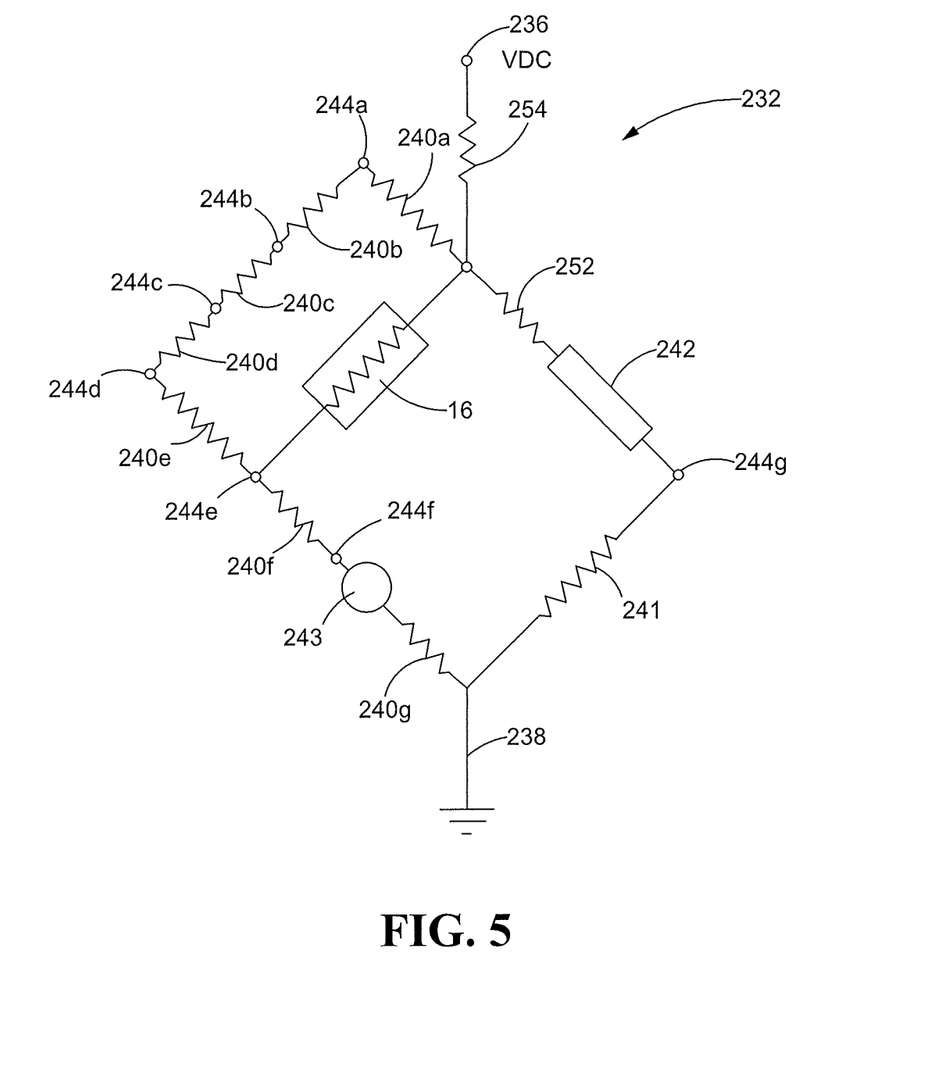
FIG. 5 is a schematic view of yet another resistance circuit.

As further shown in FIG. 5, yet another resistance circuit 232 which may employ a resistance-based inspection scheme in association with, for example, the system 24 of FIG. 3 for monitoring the wear condition of a support structure 16 of an elevator system 10 is provided. As in the previous embodiments, the resistance circuit 232 may be configured to supply a voltage across the support structure 16 via a voltage input node 236 and a ground node 238 so as to induce an electrical current therethrough. The resistance circuit 232 may further provide a first set of resistors 240 on the belt-side of the resistance circuit 232, as well as a second set of resistors 241, 242, 252 on the reference-side of the resistance circuit 232 that are electrically coupled to the support structure 16 and generally arranged in a voltage divider configuration. The first set of resistors 240 may provide output voltages on the belt-side at output nodes 244a-f which gradually increase or decrease as the support structure 16 wears over time, while the second set of resistors 241, 242, 252 may provide a reference voltage on the reference-side at output node 244g which remains constant until the next calibration. By comparing the output voltages provided by the first set of resistors 240 on the belt-side to the reference voltage provided by the second set of resistors 241, 242, 252 on the reference-side, it may be possible to determine an operational condition or state of the support structure 16 based on the change in effective resistance thereof.

Still referring to the resistance circuit 232 of FIG. 5, resistors 240a-e may be disposed in parallel to the support structure 16 while resistors 240f-g may be disposed in series to resistors 240a-e and the support structure 16. Resistors 240a-e may be configured with relatively high resistances so as to minimize its effect on the current flowing through the support structure 16. Belt-side resistors 240f-g may be disposed substantially parallel to resistor 241 on the monitor-side, and further, configured to generally match the resistance thereof. As in the previous embodiment of FIG. 4, the additional resistor 252 may be provided such that the combination of the resistor 242 and the added resistor 252 substantially matches the anticipated resistance of the belt or support structure 16. Specifically, the sum of the resistances of the second set of resistors 242, 252 may be configured to substantially match the effective resistance of the support structure 16, for example, during an initial calibration of the monitoring system 24, so as to provide the baseline or reference voltage to which the output voltages at output nodes 244*a-f* may be compared. The temperature-dependent resistor 243 may also be similarly positioned on the beltside, in series between resistors 240*f* and 240*g*, such that the combination of the temperature-dependent resistor 243 and the resistors 240*f* and 240*g* may effectively match and/or compensate for changes in the resistance of the support structure 16 caused solely by changes in ambient temperature. Furthermore, unlike in previous embodiments, the resistance circuit 232 of FIG. 5 may provide one or more additional resistors 254 disposed in-line with the voltage input node 236 and a connected voltage supply. The added resistor 254 in the resistance circuit 232 of FIG. 5 may serve to protect any connected voltage supply from short-circuit conditions which commonly occur between the tension members 26 of the support structure 16, and further, to provide a voltage drop sufficient to enable use with a single voltage supply.

Figure 6:
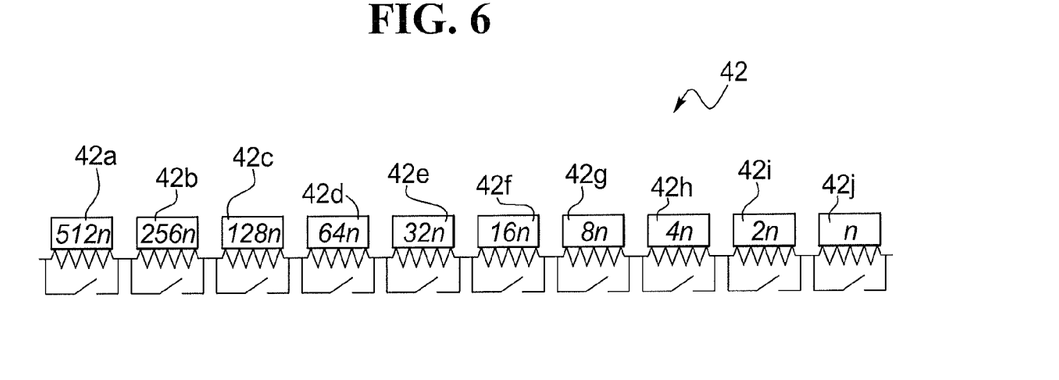
FIG. 6 is a schematic view of one exemplary set of adjustable resistors.

With reference now to FIG. 6, the second set of resistors 42 may employ a plurality of adjustable resistors 42*a-j* having varying, for example, successively decreasing, resistances that are each enabled by a dual in-line package (DIP) switch. By enabling or disabling each successive switch-enabled resistor 42*a-j*, an operator or inspector may be able to closely approximate and substantially match the effective resistance of the support structure 16 during the initial calibration. In the particular embodiment shown, the resistance of each successive resistor 42*a-j*, from the leftmost resistor 42*a* to the rightmost resistor 42*j*, may be successively decremented by a factor of one-half. Alternatively, the resistance of each adjustable resistor 42*a-j* may be varied by other factors so as to provide a lower or higher resolution of detection, respectively. In other alternatives, the second set of resistors 42 may include a greater or lesser number of switch-enabled resistors 42 to vary the resolution of detection. In still further alternatives, the second set of resistors 42 may employ one or more potentiometers or any other combination of resistors with adjustable resistances. Once correctly calibrated, the resistance circuit 32 may be configured such that any change in the effective resistance of the support structure 16, and thus any wear thereof, will result in a change in the detected voltage across or current through any of the resistors 40*a-h*, 42. Optionally, one or more of the switch-enabled resistors 42 may be temporarily or permanently sealed upon calibration so as to prohibit any further change in the resistance thereafter.

Referring back to the monitoring system 24 of FIG. 3, the interface circuit 34 may be coupled to one or more output nodes 44*a-g* of the resistance circuit 32 and employ an analog approach to continuously monitor the effective resistance of the support structure 16. More specifically, using a series of comparators 46 and light emitting diodes (LEDs) 48, the interface circuit 34 may be configured to visually provide an operator or inspector with the corresponding operational state of the support structure 16 based on any detected change in the effective resistance thereof. A change in the effective resistance of the support structure 16 may be determined, for example, by comparing the magnitudes of one or more output voltage signals of the resistance circuit 32. Based on the degree of change detected in the effective resistance of the support structure 16, one or more preconfigured thresholds may be exceeded, and further, cause one or more LEDs 48 to illuminate and/or change the color thereof according to the table of FIG. 7. Furthermore, each comparator 46 may be coupled directly to a respective LED 48 so as to immediately illuminate the LED 48 in response to an enabling condition without the involvement of a microcontroller, microprocessor, or the like. Alternatively, a plurality of the outputs of the comparators 46 may be coupled to a single LED 48 via a switched or multiplexed connection.

Figure 7:
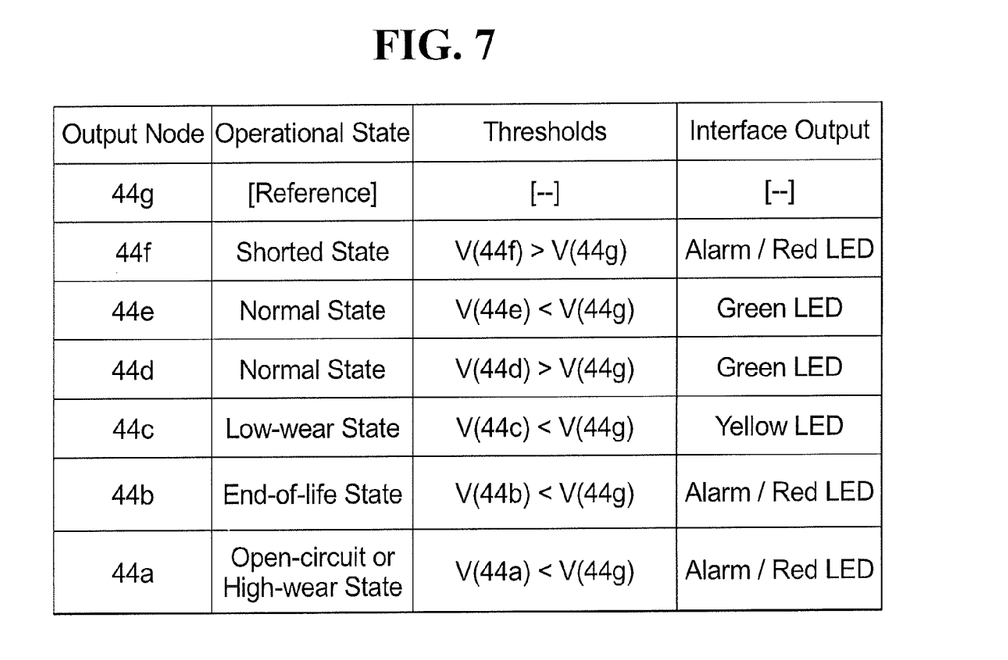
FIG. 7 is a tabular view of exemplary thresholds by which the monitoring system of FIG. 3 may operate.

According to the configuration provided in FIG. 7, one or more comparators 48 may compare the respective output voltage signals at the output nodes 44*a-f* of the resistance circuit 32 with a reference voltage signal at the output node 44*g* of, for example, the calibrated second set of resistors 42. As the support structure 16 wears, the effective resistance thereof may increase, and thus, in the resistor circuit 32 of FIG. 3, cause the voltages at output nodes 44*a-d* to decrease. Accordingly, the degree of wear of the support structure 16 may be determined by measuring the degree by which the voltages at output nodes 44*a-c* have decreased. As shown in FIG. 7, for example, if the voltage at output node 44*c* reaches a minimum threshold and falls below the voltage at output node 44*g*, the support structure 16 may be in a low-wear state. If the voltage at output node 44*a*, which is at a higher potential relative to the output node 44*c*, reaches a minimum threshold and falls below the voltage at output node 44*g*, the support structure 16 may be at a more critical open-circuit or high-wear state. In a similar fashion, the interface circuit 34 may also be preconfigured with thresholds to monitor for one or more of a normal state, a calibrated state, a shorted state, an end-of-life state, and the like.

Still referring to FIG. 7, once a threshold is exceeded, the corresponding comparator 46 may enable a respective LED 48 to illuminate and indicate to an operator or inspector of the respective operational state. For example, if the output voltage signal at the output node 44*b* falls below the threshold of the output voltage signal at output node 44*g*, the corresponding LED 48 may illuminate in red to indicate or warn that the support structure 16 is in an end-of-life state. The interface circuit 34 may optionally or additionally provide an audible alarm 50, such as a buzzer, ringer, or the like, that is further enabled by the associated comparator 46 so as to call attention to the monitoring system 24. Alternatively, the interface circuit 34 may further include a microcontroller configured to manage the illumination of one or more LEDs 48 based on the output signals, transmit alert notifications to a mobile device, display alert notifications at a monitor of a remote monitoring station, and the like. In still further modifications, the comparators 46 of FIG. 3 may further be configured to provide one or more control signals to the controller 22 of the elevator system 10 so as to, for instance, temporarily cease operation of the elevator system 10 in response to a detected fault or when a threshold has been exceeded. The control signals may be transmitted using discrete signals, serial communication, controller area network (CAN) bus, or any other suitable communication means. Alternatively, the interface circuit 34 may be configured to control a state of one or more relays of, for example an elevator safety chain, based on and/or in response to the output signals provided by the comparators 46. In such a way, the interface circuit 34 may communicate the operational state to, for example a controller 22, of the elevator system 10.

Figure 8:
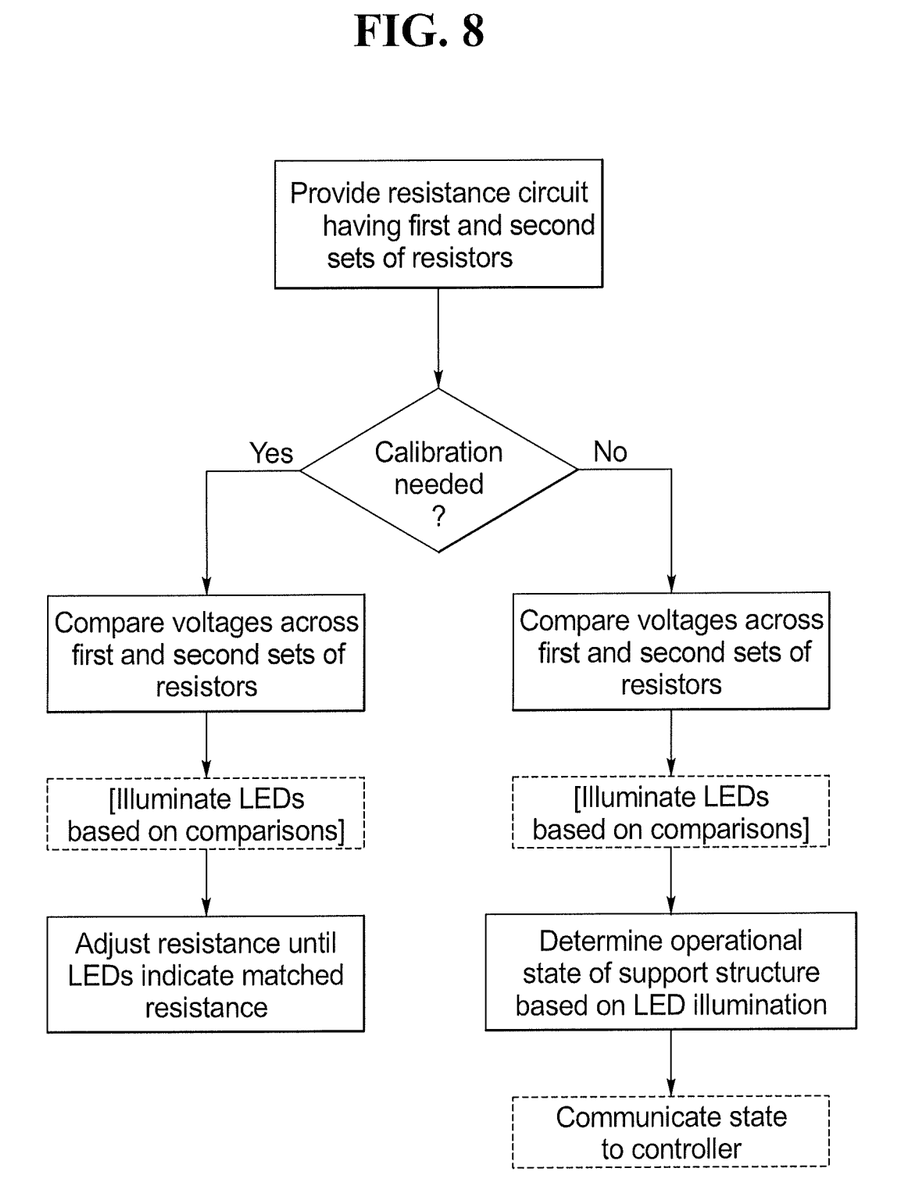
FIG. 8 is a diagrammatic view of a method for monitoring a support structure of an elevator system and a method for calibrating a resistance-based inspection system.

Turning now to FIG. 8, a flow diagram illustrating an exemplary method for monitoring a support structure 16 of an elevator system 10 as well as a method for calibrating a monitoring system 24 is provided. As an initial step, both methods may provide a resistance circuit 32 having a first set of resistors 40 and a second set of resistors 42 coupled to the support structure 16. In an optional step, an interface circuit 34 having a plurality of comparators 46 for comparing the voltages across the respective resistors 40, 44 may also be provided. An additional step may determine if calibration is needed, for example, if the support structure 16 is newly installed, if the support structure 16 has been recently replaced, or the like. If calibration is needed, one or more voltages across the first set of resistors 40 may be compared with a voltage across the second set of resistors 42 so as to determine the degree by which the electrical load or effective resistance of the support structure 16 matches the resistance of the second set of resistors 42. With respect to the configuration of FIG. 7, for example, each of the output voltage signals at output nodes 44*e*-*d* may be compared with the reference voltage signal at output node 44*g*. If the reference voltage signal at output node 44*g* is greater than the output voltage signal at output node 44*d* or less than the output voltage signal at output node 44*e*, one or more LEDs 48 may be illuminated to indicate that adjustment of the second set of resistors 42 is needed. For example, if the voltage at output node 44*g* is greater than the voltage at output node 44*d*, a first LED 48 corresponding to the third threshold in FIG. 7 may illuminate in green while a second LED 48 corresponding to the fourth threshold in FIG. 7 may be completely off or illuminated in a different color. Alternatively, if the voltage at output node 44*g* is less than the voltage at output node 44*e*, the first LED 48 may be completely off or illuminated in a different color while the second LED 48 is illuminated in green. If the resistance of the second set of resistors 42 sufficiently matches the effective resistance of the support structure 16, and if the voltage at output node 44*g* is measured to be between the upper and lower limits of the voltages at output nodes 44*d*-*e*, respectively, both first and second LEDs 48 may be illuminated in green so as to indicate a successful calibration. In such a way, the resistance of the second set of resistors 42 may enable incremental adjustments of the second set of resistors 42 until both first and second LEDs 48 illuminate in green and indicate that the effective resistance of the support structure 16 is matched.

Once calibration is complete, or if calibration is not needed, the method for monitoring a support structure in FIG. 8 may also include a step of comparing one or more voltages across the first set of resistors 40 with a voltage across the second set of resistors 42. This is so as to determine the degree by which the effective resistance of the support structure 16 has diverged from the resistance initially matched by the second set of resistors 42 during calibration. Referring to the configuration set out in FIG. 7, for example, each of the output voltage signals at output nodes 44*a*-*f* may be compared with the reference voltage signal at output node 44*g*. If any of the voltages at output nodes 44*a*-*f* rises above or falls below the reference voltage signal according to the respective thresholds as provided in FIG. 7, one or more LEDs 48 may be illuminated to indicate the operational state of the support structure 16 corresponding to the exceeded thresholds. For example, if the voltage at output node 44*f* is greater than the voltage at output node 44*g*, one or more LEDs 48 corresponding to the first threshold of FIG. 7 may be illuminated in red to indicate a shorted state, or when one or more tension members 26 of the support structure 16 are improperly in contact with one another. Accordingly, the immediate wear condition or operational state of the support structure 16 may be determined based on the continuous feedback provided by the illuminated LEDs 48.

Figure 9:
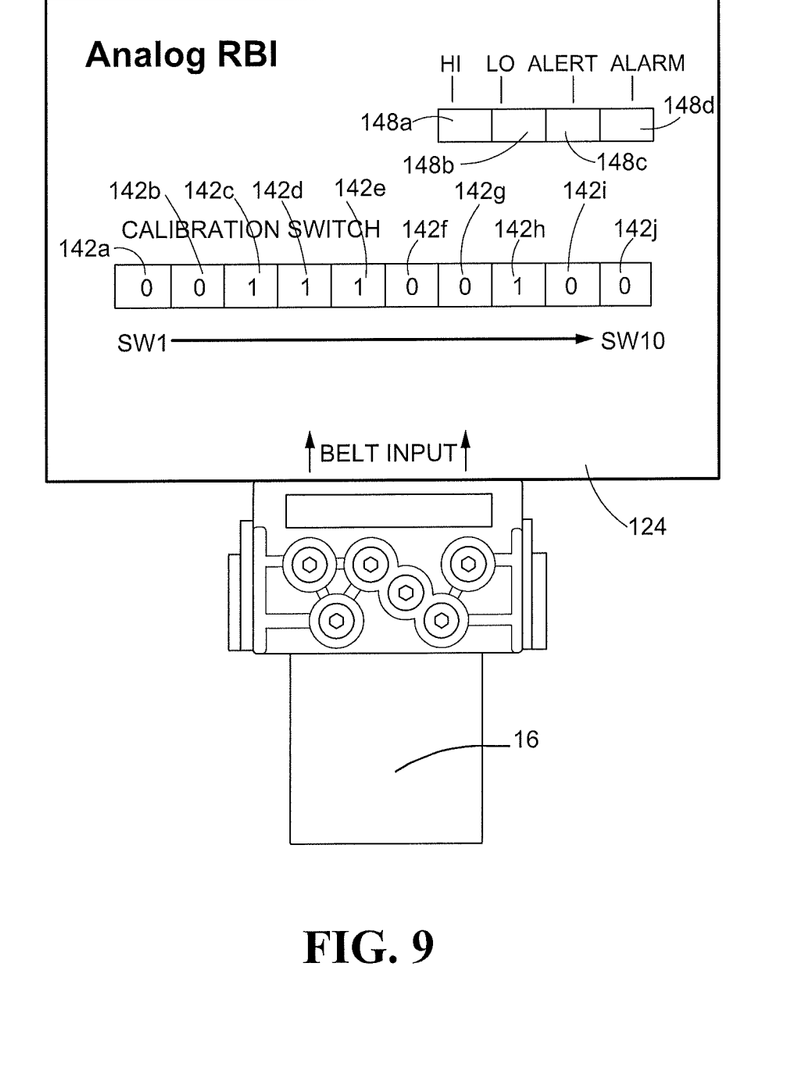
FIG. 9 is a graphical view of another monitoring system.

Referring now to FIG. 9, another exemplary embodiment of a system 124 for monitoring the wear condition of a support structure 16 of an elevator system 10 is provided. Similar to the embodiment of FIG. 6, the monitoring system 124 may include a plurality of selectively engageable calibration switches (SW1-SW10) 142*a-j*, provided in the form of DIP switches, or the like, where each switch 142*a-j* corresponds to a different resistance value. In addition, the calibration switches 142*a-j* may be configured such that each switch 142*a-j* is successively aligned from left to right in a manner of decreasing resistance. Moreover, the resistance of each successive switch 142*a-j* may be decreased by a factor of one-half, where the leftmost switch 142*a* corresponds to the greatest value of selectable resistance (i.e., 512*n*) and the rightmost switch 142*j* corresponds to the least value of resistance (i.e., n).

The monitoring system 124 of FIG. 9 may further provide a plurality of LEDs 148*a-d* configured to aid a user or operator during a calibration of the monitoring system 124 and/or to indicate the operational condition or wear state of the associated support structure 16. More specifically, the HI and LO LEDs 148*a-b* of FIG. 9 may be used in combination with one another to help match the effective resistance of a newly installed support system 16 during a calibration stage, as will be discussed in more detail further below. The ALERT LED 148*c* may be used to indicate a warning with respect to the wear state of the attached support structure 16, or a condition in which the support structure 16 is operational but nearing a critical wear state. Correspondingly, the ALARM LED 148*d* may be used to indicate a more urgent or critical condition in which the support structure 16 is significantly worn, unusable and in need of immediate replacement. In further modifications, the monitoring system 124 may be configured such that triggering of the ALARM LED 148*d* may further trigger a connected relay, or the like, to shut down normal elevator operation and/or engage other alert or notification systems. In still further modifications, the monitoring system 124, and/or an interface circuit 34 associated therewith, may be electrically coupled to a plurality of support structures 16 sharing and/or in communication with a common or series-type relay output.

Figure 10:
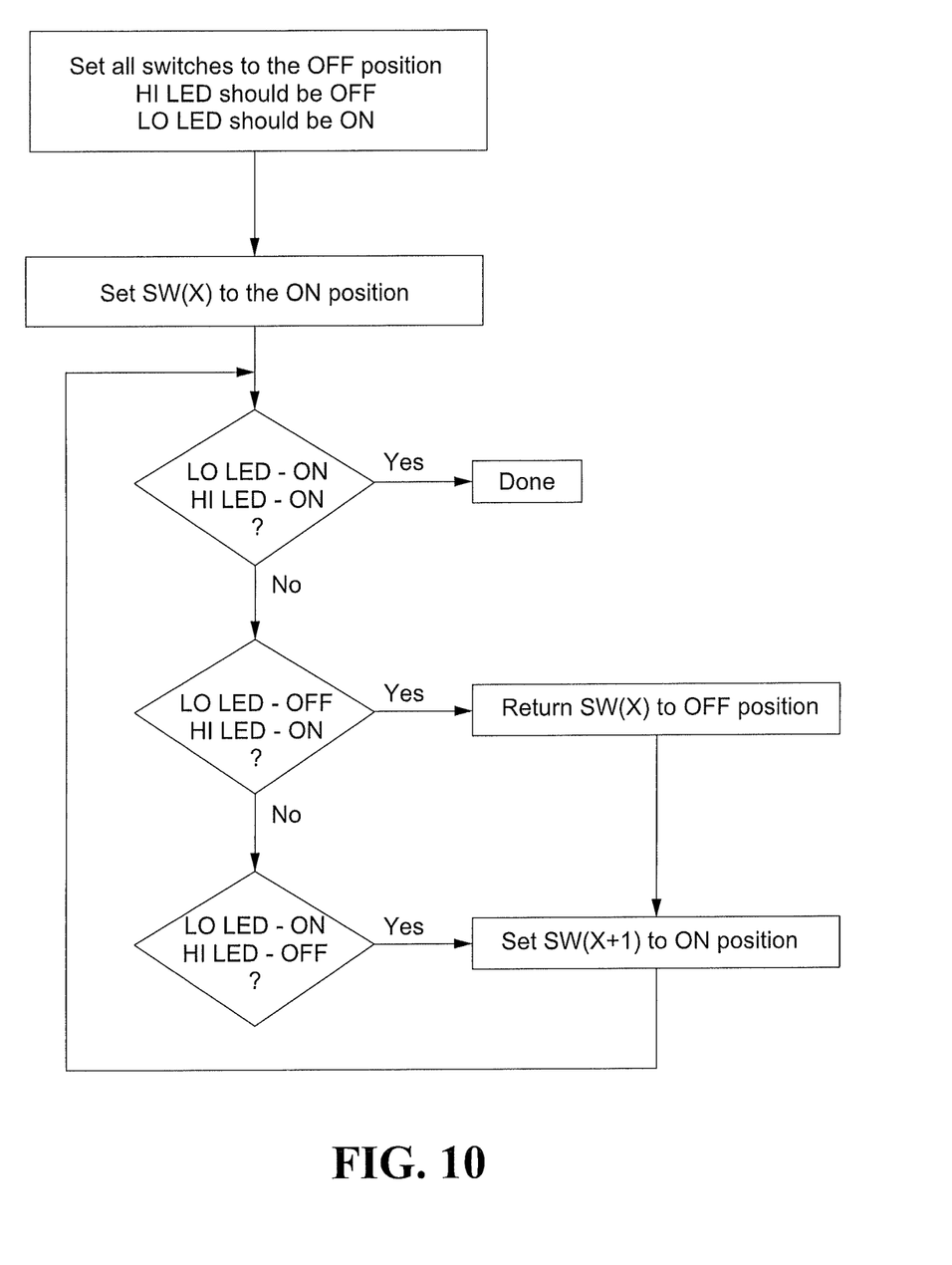
FIG. 10 is a diagrammatic view of another method for calibrating a resistance-based inspection system.
Figure 11A:
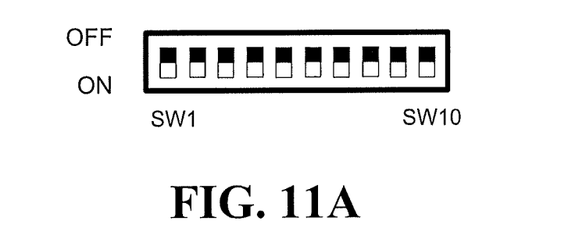
FIG. 11A is a graphical view of another set of adjustable resistors prior to calibration.
Figure 11B:
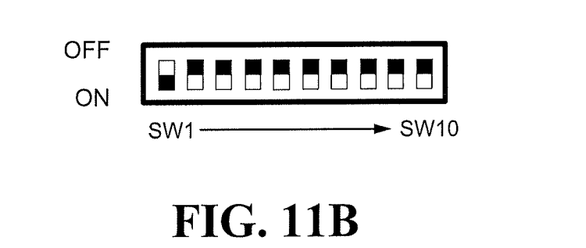
FIG. 11B is a graphical view of the adjustable resistors of FIG. 11A with a first switch enabled.

Upon each installation of a new belt or support structure 16, the monitoring system 124 of FIG. 9 may be calibrated according to, for example, the method disclosed in FIG. 10. Initially, all of the switches (SW1-SW10) 142*a-j* may be set to the OFF position, as shown for example by the DIP switches in FIG. 11A. At this point, the HI LED 148*a* on the monitoring system 124 of FIG. 9 should be unlit or turned off and the LO LED 148*b* should be lit or turned on. In a subsequent step, the leftmost switch (SW1) 142*a*, or the switch corresponding to the greatest resistance value, may be switched into the ON position, as shown for example in FIG. 11B. If both the HI LED 148*a* and the LO LED 148*b* are turned on, this may be an indication that the effective resistance of the newly installed support structure 16 is substantially matched by the collective resistance of the resistors 142*a j*, or in combination with any added resistors 152, and thus, an indication that the calibration sequence is complete. No further adjustments may be necessary.

Figure 11C:
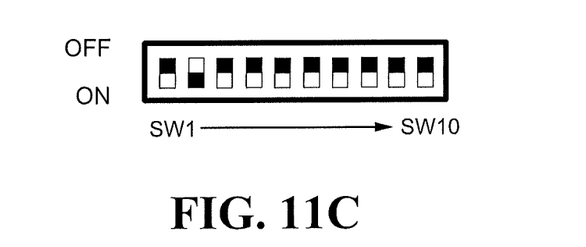
FIG. 11C is a graphical view of the adjustable resistors of FIG. 11A with the first switches disabled and the second switch enabled.

If, however, the HI LED 148*a* is turned on and the LO LED 148*b* is turned off, this may be an indication that the collective resistance of the resistors 142*a-j* overshoots the effective resistance of the support structure 16. Accordingly, the current switch (SW1) 142*a* may then be returned back to the OFF position and the next switch (SW2) 142*b* in the sequence may be switched to the ON position, as shown for example in FIG. 11C. Alternatively, if the HI LED 148a is turned off and the LO LED 148b is turned on, this may be an indication that the collective resistance of the resistors 142a-j undershoots the effective resistance of the support structure 16. In this condition, the first switch (SW1) 142a may be maintained in the ON position while the next switch (SW2) 142b in succession may be switched to the ON position. This calibration process may be repeated for each successive switch until both HI and LO LEDs 148a-b are lit and/or until the final switch (SW10) 142j in the sequence has been tested.

Furthermore, once calibration is complete, the switches (SW1-SW10) 142a-j may be at least temporarily sealed, for example, using a removable tape, a sticker, a casing, or any other suitable tamperproof seal, configured to prevent accidental or improper reconfiguration of the switches (SW1-SW10) 142a-j until a subsequent calibration is required, such as when a new support structure 16 is installed. Moreover, the seal may be transparent such that maintenance personnel may easily view the prior calibration settings as reference without needing to remove the seal.

Based on the foregoing, it can be seen that the present disclosure may provide a system and method for monitoring support structures of an elevator system with minimal complexity and more cost-effective implementations. The present disclosure may also provide continuous monitoring of support structures and enable immediate responses to detected fault conditions. Furthermore, the present disclosure provides a system and method which allows for easier and more accurate calibrations thereof.

While only certain embodiments have been set forth, alternatives and modifications will be apparent from the above description to those skilled in the art. These and other alternatives are considered equivalents and within the spirit and scope of this disclosure.

What is claimed is:

1. A resistance circuit for monitoring a support structure, comprising:
    a voltage input node to supply a voltage;
    a first set of resistors disposed at a belt-side of the structure and configured to indicate one or more voltages thereacross corresponding to an effective resistance of the support structure, the first set of resistors including at least one temperature-dependent resistor;
    the first set of resistors including at least two resistors in series and coupled to the voltage input node, the at least two resistors in series being in parallel with the effective resistance of the support structure; and
    a second set of resistors disposed at a monitor-side of the structure and configured to indicate one or more voltages thereacross corresponding to an initial effective resistance of the support structure, the second set of resistors including at least one switched resistor having an adjustable resistance capable of selectively approximating the initial effective resistance;
    wherein the first set of resistors is disposed at least partially in parallel relative to the effective resistance of the support structure and the temperature-dependent resistor is disposed in series relative to the effective resistance of the support structure, the temperature-dependent resistor being disposed in series with at least one fixed-resistance resistor, the temperature-dependent resistor and the fixed-resistance resistor being configured to approximate a temperature coefficient of a plurality of tension members disposed within the support structure.

2. The resistance circuit of claim 1, wherein the first set of resistors provides a plurality of voltages thereacross, each voltage providing a different threshold for detecting a potential difference over a plurality of tension members within the support structure.

3. The resistance circuit of claim 1, wherein the second set of resistors includes a plurality of switched resistors, each switched resistor being series-connected to a successive switched resistor with a selectable resistance value that is decremented by a factor of one-half.

4. The resistance circuit of claim 1, wherein the second set of resistors includes a dual in-line package (DIP) of series-connected switched resistors capable of approximating the initial effective resistance of the support structure upon calibration.

5. The resistance circuit of claim 1, wherein the at least one switched resistor further includes a seal thereover configured to substantially prevent further adjustment of the at least one switched resistor upon calibration and until subsequent calibration is required, the seal enabling reference to calibrated settings without removal thereof.

6. The resistance circuit of claim 1, further comprising one or more comparators configured to compare the one or more voltages across the first set of resistors on the belt-side corresponding to the effective resistance of the support structure, with the one or more voltages across the second set of resistors on the monitor-side corresponding to the initial effective resistance of the support structure.

7. A monitoring system for a support structure, comprising:
    a voltage input node to supply a voltage, the voltage applied to the support structure;
    a resistance circuit coupled to an effective resistance of the support structure, the resistance circuit having a first set of resistors and at least one temperature-dependent resistor disposed on a belt-side, and a second set of resistors and at least one switched resistor on a monitor-side, the second set of resistors being coupled to the voltage input node, the support structure including a plurality of tension members;
    the first set of resistors including at least two resistors in series and coupled to the voltage input, the at least two resistors in series being in parallel with the effective resistance of the support structure; and
    an interface circuit having two or more comparators coupled to the resistance circuit and configured to monitor a wear level of the support structure based on a comparison between a voltage across at least one of the first resistors and a reference voltage across at least one of the second resistors corresponding to an initial effective resistance of the support structure, and generate one or more output signals based on the comparison.

8. The monitoring system of claim 7, wherein the monitoring system further comprising at least one series-connected resistor disposed between the voltage input node and the resistance circuit, the at least one series-connected resistor being configured to provide a voltage drop sufficient for use with the voltage input node and protect the voltage input node from short-circuit conditions within the plurality of tension members of the support structure.

9. The monitoring system of claim 7, wherein the first set of resistors is disposed at least partially in parallel relative to the support structure and the temperature-dependent resistor is disposed in series relative to the support structure, the temperature-dependent resistor being disposed in series with at least one fixed-resistance resistor, the temperature-dependent resistor and the fixed-resistance resistor being configured to approximate a temperature coefficient of the plurality of tension members disposed within the support structure.

10. The monitoring system of claim 7, wherein the second set of resistors includes a plurality of switched resistors, each switched resistor being series-connected to a successive switched resistor with a selectable resistance value that is decremented by a factor of one-half.

11. The monitoring system of claim 7, wherein the second set of resistors includes a dual in-line package (DIP) of series-connected switched resistors capable of approximating the initial effective resistance of the support structure upon calibration.

12. The monitoring system of claim 7, wherein the at least one switched resistor further includes a seal thereover configured to substantially prevent further adjustment of the at least one switched resistor upon calibration and until subsequent calibration is required, the seal enabling reference to calibrated settings without removal thereof.

13. The monitoring system of claim 7, wherein the interface circuit is electrically coupled to a plurality of support structures sharing a common, series-type relay output.

14. The monitoring system of claim 7, wherein the interface circuit includes one or more light emitting diodes LEDs configured to indicate one or more operational conditions of the support structure based on the detected wear level.

15. A method for calibrating a resistance-based monitoring system for a support structure, the method comprising:
configuring a resistance circuit that is coupled to an effective resistance of the support structure to provide a first set of resistors and at least one temperature-dependent resistor disposed on a belt-side, and a second set of resistors and a plurality of series-connected switched resistors on a monitor-side, the support structure including a plurality of tension members;
the first set of resistors including at least two resistors in series and coupled to a voltage input node, the at least two resistors in series being in parallel with the effective resistance of the support structure;
for each consecutive one of the series-connected switched resistors:
enabling the series-connected switched resistor;
comparing a resistance on the belt-side of the resistance circuit with a resistance on the monitor-side of the resistance circuit, the belt-side resistance corresponding to an effective resistance of the support structure;
enabling a consecutive one of the series-connected switched resistors if the belt-side resistance is greater than the monitor-side resistance; and
enabling a consecutive one of the series-connected switched resistors and disabling the series-connected switched resistor if the belt-side resistance is less than the monitor-side resistance.

16. The method of claim 15, further comprising sealing the plurality of series-connected switched resistors with a seal once calibration is complete, the seal enabling reference to calibrated settings without removal thereof, the calibration being complete when the belt-side resistance substantially approximates the monitor-side resistance.

17. The method of claim 15, wherein one or more LEDs are configured to indicate the comparisons between the belt-side resistance and the monitor-side resistance.

18. The method of claim 15, wherein a resistance of each successive series-connected switched resistor is decremented by a factor of one-half.

19. The method of claim 15, wherein the temperature-dependent resistor is disposed in series relative to the support structure, the temperature-dependent resistor being disposed in series with at least one fixed-resistance resistor, the temperature-dependent resistor and the fixed-resistance resistor being configured to approximate a temperature coefficient of the plurality of tension members disposed within the support structure.

* * * * *